(12) United States Patent
Lenna et al.

(10) Patent No.: US 9,556,220 B2
(45) Date of Patent: Jan. 31, 2017

(54) PROCESS FOR THE PREPARATION OF DROSPIRENONE

(71) Applicant: INDUSTRIALE CHIMICA S.R.L., Milan (IT)

(72) Inventors: Roberto Lenna, San Giorgio su Legnano (IT); Francesco Barbieri, Masciago (IT); Maria Giovanna Luoni, Cardano al Campo (IT); Monica Noseda, Como (IT)

(73) Assignee: INDUSTRIALE CHIMICA S.R.L. (IT)

( * ) Notice: Subject to any disclaimer, the term of this patent is extended or adjusted under 35 U.S.C. 154(b) by 0 days.

(21) Appl. No.: 14/783,830

(22) PCT Filed: Apr. 12, 2013

(86) PCT No.: PCT/IB2013/052918
§ 371 (c)(1),
(2) Date: Oct. 9, 2015

(87) PCT Pub. No.: WO2014/167386
PCT Pub. Date: Oct. 16, 2014

(65) Prior Publication Data
US 2016/0052960 A1 Feb. 25, 2016

(51) Int. Cl.
*C07J 53/00* (2006.01)
(52) U.S. Cl.
CPC .................................. *C07J 53/008* (2013.01)
(58) Field of Classification Search
CPC ....... C07J 21/003; C07J 53/001; C07J 53/007; C07J 53/008
USPC .......................................................... 540/15
See application file for complete search history.

(56) References Cited

U.S. PATENT DOCUMENTS

| 4,416,985 | A | 11/1983 | Petzoldt et al. |
| 6,933,395 | B1 | 8/2005 | Mohr et al. |

FOREIGN PATENT DOCUMENTS

| CN | 101503455 | 8/2009 |
| EP | 0075189 | 3/1983 |
| EP | 0918791 | 4/2002 |
| EP | 1571153 | 3/2010 |
| EP | 1828222 | 12/2010 |

(Continued)

OTHER PUBLICATIONS

PCT Search Report and Written Opinion dated Jan. 7, 2014 for PCT/IB2013/052918 entitled Process for the Preparation of Drospirenone filed on Apr. 23, 2013.

Schultz, Mitchell et al, A Convenient Palladium-catalyzed Aerobic Oxidation of Alcohols at Room Temperature; Chem Comm (www.rsc.org/chemcomm) The Royal Society of Chemistry, pp. 3034-3035, 2002.

(Continued)

*Primary Examiner* — Brenda Coleman
(74) *Attorney, Agent, or Firm* — Fish & Tsang, LLP

(57) ABSTRACT

A process is disclosed wherein, using either 17a-(3-hydroxy-propyl)-6p,7p;15p,16p-dimethylene-5p-androstane-3p,5,17p-triol (II) or 3β,5^ïl^κ^-6β,7β;15β,16β-dimethylene-5β,17α-pregnane-21,17-carbolactone (III) as starting material, through a single-step reaction it is obtained drospirenone (I), a synthetic steroid with progestogenic, antimineralocorticoid and antiandrogenic activity, useful for preparing pharmaceutical compositions with contraceptive action.

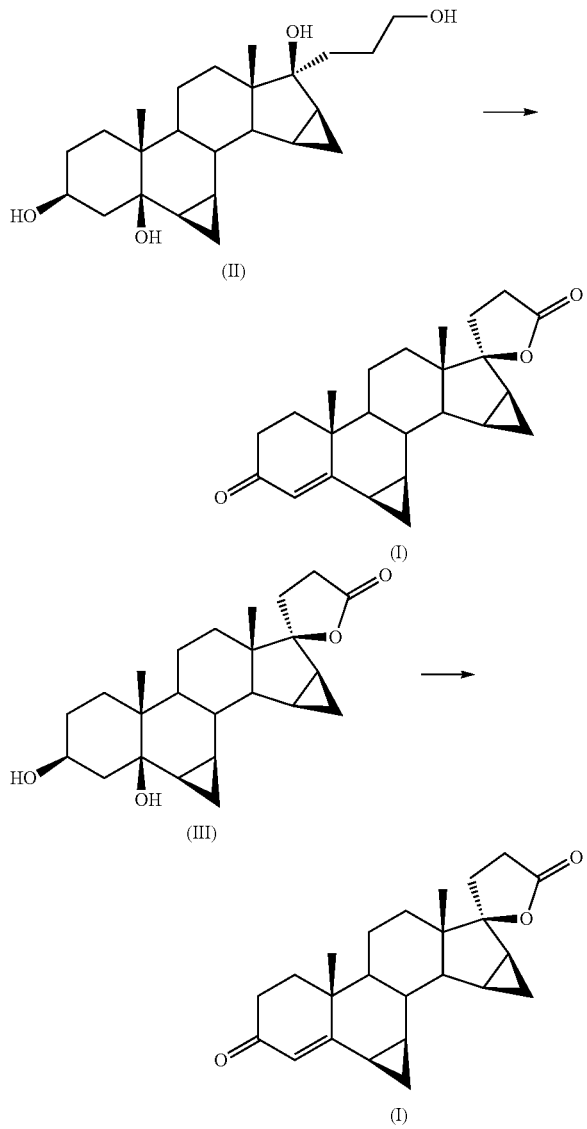

11 Claims, No Drawings

(56) References Cited

FOREIGN PATENT DOCUMENTS

WO    2010146042    12/2010

OTHER PUBLICATIONS

Nishimura, Takahiro et al, Palladium(II)-Catalyzed Oxidation of Alcohols to Aldehydes and Ketones by Molecular Oxygen, J. Org. Chem. 1999, 64, pp. 6750-6755.

Ito et al., Synthesis of α,β-Unsaturated Carbonyl Compounds by Palladium(II)-Catalyzed Dehydrosilylation of Silyl Enol Ethers, J. Org. Chem., 1978, vol. 43, No. 5, pp. 1011-1013.

PROCESS FOR THE PREPARATION OF DROSPIRENONE

FIELD OF THE INVENTION

The present invention relates to the field of processes for the synthesis of steroids and, in particular, to a process for preparing drospirenone on an industrial scale.

BACKGROUND ART

The compound of formula (I) below, whose chemical name is 6β,7β;15β,16β-dimethylen-3-oxo-17α-pregn-4-ene-21,17-carbolactone, is commonly referred to as drospirenone:

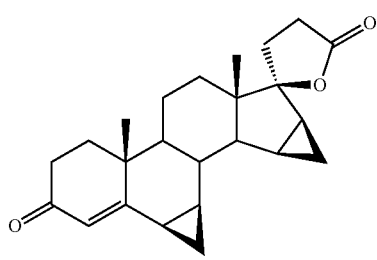

(I)

Drospirenone is a synthetic steroid with progestogenic, antimineralocorticoid and antiandrogenic activity; by virtue of these properties it has long been used for preparing pharmaceutical compositions with contraceptive action for oral administration.

Various processes are known in the literature for preparing drospirenone.

The process described in European Patent EP 075189 B1 obtains the final product drospirenone through oxidation under heating of 17α-(3-hydroxypropyl)-6β, 7β,15β,16β-dimethylene-5β-androstane-3β,5,17β-triol with a mixture of pyridine/water/chromium(VI) oxide. This step represents a substantial drawback in the process: in fact, chromium(VI) oxide, like all Cr(VI) compounds, is an established carcinogen, the use of which is subject to such legislative restrictions that the precautions required during use and disposal of this product led to abandonment of the above industrial process.

A similar situation occurs with the process of U.S. Pat. No. 4,416,985, wherein drospirenone is obtained through oxidation under heating of 3β,5-dihydroxy-6β,7β;15β,16β-dimethylene-5β,17α-pregnane-21,17-carbolactone using a mixture of pyridine/water/chromium(VI) oxide.

Another process for preparing drospirenone is described in European Patent EP 918791 B8; in the process of this document drospirenone is obtained, still from 17α-(3-hydroxypropyl)-6β,7β,15β,16β-dimethylen-5β-androstan-3β,5,17β-triol, in two distinct steps and by using an oxidant such as e.g. potassium bromate in the presence of ruthenium salts as catalysts, which eventually must be completely removed from the product.

European patent EP 1828222 B1 discloses a further process, where the oxidation step is carried out using calcium hypochlorite as an oxidant in the presence, as catalyst, of the 2,2,6,6-tetramethylpiperidine-1-oxyl radical or a derivative thereof; in the process of this patent the oxidant is added in portions until completion of the reaction. This process overcomes the disadvantages of the prior art in that calcium hypochlorite is a non-carcinogenic reagent, nor is 2,2,6,6-tetramethylpiperidine-1-oxyl radical a metal catalyst requiring purification of the final product; however, the need for sequential reagent additions and analytical controls in the course of reaction, while being simple, hamper standardized production that should run continuously or nearly so. As a result, the method of this patent too has process drawbacks with regard to industrial production.

Thus, there is a continuing need for a simple process for drospirenone production which allows to overcome prior art limitations.

Hence, it is the purpose of the present invention to provide an industrial process which allows preparing drospirenone without using reagents that are either dangerous or whose use is restricted by industry regulations, and minimizing operator intervention during the process itself.

SUMMARY OF THE INVENTION

This purpose is achieved by the present invention, which relates to a process for the production of drospirenone comprising the single-step conversion of a compound selected from 17α-(3-hydroxypropyl)-6β,7β,15β,16β-dimethylen-5β-androstan-3β,5,17β-triol and 3β,5-dihydroxy-6β,7β;15β,16β-dimethylen-5β,17α-pregna-21,17-carbolactone using gaseous oxygen in the presence of a compound of palladium in the +2 oxidation state, an organic base and molecular sieves in an organic solvent inert under the reaction conditions, at a temperature between 60 and 140° C. In case of using 17α-(3-hydroxypropyl)-6β,7β,15β,16β-dimethylen-5β-androstan-3β,5,17β-triol, having formula (II) below, the compound can be in mixture with one or both of its lactols, as described in Example 6 of patent EP 1828222 B1 above. The reaction scheme (reaction scheme 1) is as follows, where lactols are shown in parentheses to indicate that they may or may not be present, and the symbol in the formula of lactols indicates that the —OH group can be found either above or below the molecule plane (i.e., in β- or α-configuration, respectively):

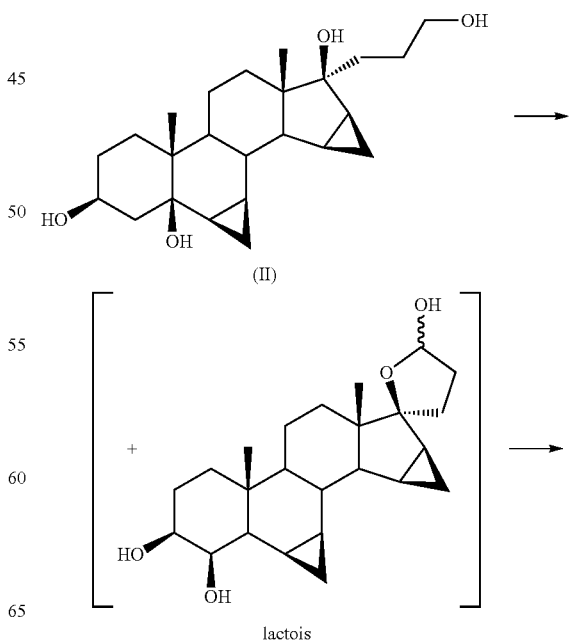

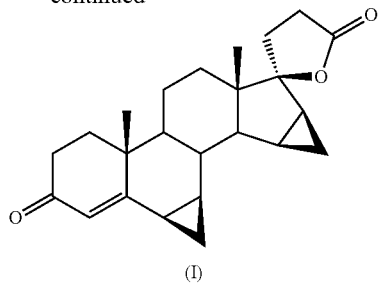

(I)

Said reaction allows obtaining drospirenone directly, in a single process step, eliminating the need for subsequent additions of further reagents to complete the conversion.

In case of using 3β,5-dihydroxy-6β,7β;15β,16β-dimethylen-5β,17α-pregna-21,17-carbolactone (of formula (III) below) as starting compound, the reaction takes place according to the following scheme (reaction scheme 2):

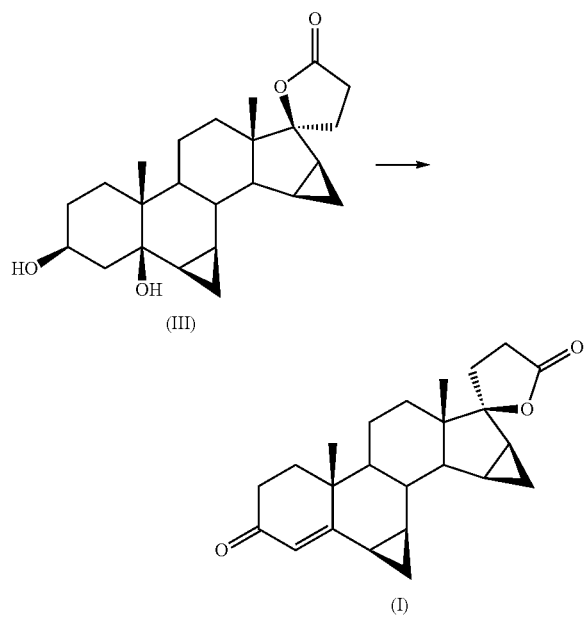

Features and advantages of the present process will be apparent from the following detailed description.

DETAILED DESCRIPTION OF THE INVENTION

The Applicant has developed an extremely simple novel process, which allows obtaining drospirenone from 17α-(3-hydroxypropyl)-6β,7β,15β,16β-dimethylen-3β,5,17β-triol (II) or from 3β,5-dihydroxy-6β,7β;15β,16β-dimethylen-5β,17α-pregna-21,17-carbolactone (III) using oxygen in the presence of a system comprising a compound of palladium in the +2 oxidation state, an organic base, and molecular sieves in a non-oxidizable organic solvent.

The first possible reaction substrate of the present process, i.e. the compound 17α-(3-hydroxypropyl)-6β,7β,15β,16β-dimethylen-5β-androstan-3β,5,17β-triol (II) (or a mixture thereof with the corresponding lactols) can be obtained from commercially available products using procedures known to the person skilled in the art. Preferably, said compound is obtained according to steps a) to f) of the process described in patent EP 1828222 B1.

The second possible reaction substrate of the process, i.e. the compound 3β,5-dihydroxy-6(3,7β;15β,16β-dimethylen-5β,17α-pregna-21,17-carbolactone (III), can be obtained according to the procedure described in Example 5(b) of U.S. Pat. No. 4,416,985.

Reaction conditions as described in the following apply regardless of whether one starts from compound (II) or from compound (III).

The first component of the oxidizing system of the invention is gaseous oxygen. Gaseous oxygen gas can be supplied into the reaction vessel as pure oxygen, air, or a synthetic mixture of oxygen with an inert gas (e.g. the so-called synthetic air, which is widely used in the medical field); oxygen, in any of the above forms, can be used under static conditions, i.e. within a closed container in oxygen or oxygen-containing atmosphere, or under mild flow conditions in the same gaseous atmosphere. Working pressure is between room pressure (1 bar) and 10 bar.

The second component of the oxidizing system is a derivative of palladium in the +2 oxidation state, which is used in amounts by weight ranging from 1% to 100% with respect to the oxidation substrate.

Examples of palladium compounds suitable for the purposes of the invention include acetate $(Pd(C_2H_3O_2)_2)$, acetylacetonate $(Pd(C_5H_7O_2)_2)$, trifluoroacetate $(Pd(C_2O_2F_3)_2)$, hexafluoroacetylacetonate $(Pd(C_5HO_2F_6)_2)$, propionate $(Pd(C_3H_5O_2)_2)$, chloride $(PdCl_2)$, bromide $(PdBr_2)$, iodide $(PdI_2)$, cyanide $(Pd(CN)_2)$, nitrate $(Pd(NO_3)_2)$, sulfide $(PdS)$, oxide $(PdO)$ and hydroxide $(Pd(OH)_2)$; among those compounds acetate is preferred, which will also be referred to hereinafter as $Pd(OAc)_2$, the common abbreviation used in chemistry.

The third component of the oxidizing system is an organic base which can be selected from: pyridine and its alkyl derivatives, triethylamine, aniline, pyrrolidine, DBU (1,8-Diazabicyclo[5.4.0]undec-7-ene), DBN (1,5-Diazabicyclo[4.3.0]non-5-ene), and cyclic compounds containing two or more nitrogen atoms, both aromatic and non-aromatic; the preferred base is pyridine. The amount by weight of the organic base used is at least 0.5-fold compared with the amount of palladium compound, and preferably between 0.5 and 25 times as much as the amount by weight of said compound.

Molecular sieves that can be used are those of common commercial availability with pore diameter of 3, 4 and 5 Angstroms, preferably 3 Angstrom-type (3A sieves) both as fine powder and in form of beads or pellets.

As a solvent for the reaction an organic solvent can be used that is necessarily inert under reaction conditions, with boiling point of at least 60° C. Such a solvent can be selected from methyl t-butyl ether, ethyl acetate, isopropyl acetate, butyl acetate, heptane, hexane, cyclohexane, toluene, xylene, 1,1-dichloroethane, 1,2-dichloroethane, 1,1,2-trichloroethane, tetrachloroethylene, methyl ethyl ketone, methyl isobutyl ketone, acetonitrile, dimethylformamide, dimethylacetamide, dimethyl sulfoxide, chlorobenzene, N-methyl-pyrrolidone or mixtures thereof.

The reaction can be carried out at a temperature ranging between 60 and 140° C., preferably between 80 and 120° C., for a period of time between 18 and 72 hours, preferably between 20 and 60 hours.

Crude drospirenone as obtained through the present process can be purified by techniques known to those skilled in the art and disclosed in publications and patents; for example, purification can be achieved by crystallization from isopropyl acetate, as described in patent EP 1828222 B1, or by chromatography as described in EP 75189.

Potential formation of 1,2-dehydrodrospirenone as an impurity resulting from dehydrogenation of drospirenone positions 1 and 2 can be easily overcome by converting this impurity back into drospirenone through hydrogenation with palladium on carbon in an organic solvent such as tetrahydrofuran; hydrogenation can be performed on the reaction mixture as such after oxygen removal or on the recovered product.

Alcohol oxidation by Pd(OAc)$_2$ is known and described in the paper "Palladium(II)-Catalyzed Oxidation of Alcohols to Aldehydes and Ketones by Molecular Oxygen", T. Nishimura et al., J. Org. Chem. 1999, 64, 6750-6755. After reading this paper, however, a chemist with the aim of synthesizing drospirenone from one of the starting compounds of formula (II) or (III) above, would not have been directed to apply the method described in said paper.

In fact, the process leading to drospirenone formation from intermediate (II) involves three oxidation steps, one cyclization and one dehydration that have to occur in a specific order to yield the desired compound, as depicted in the diagram below:

nyl compounds by palladium(II)-catalyzed dehydrosilylation of silyl enol ethers", Y. Ito et al., J. Org. Chem. 1978, Vol 43 (5) on page 1021, entry 12.

The above mentioned paper by T. Nishimura et al. discloses in Table 3 examples of aliphatic primary alcohols oxidation, leading exclusively to aldehydes. Table 4 in the paper shows examples of oxidation of diols into lactones; in particular symmetrical diols (entry 1, 2, 3) and an asymmetric diol (entry 4); examples relevant to the present invention are not disclosed, i.e. relating to oxidation of an asymmetrical diol wherein one of the two OH groups is tertiary and thus subject to reactions of tertiary alcohols, including dehydration. Table 5 in the paper shows oxidation of secondary alcohols. Example 7 relates to a steroid in which however the only functional group is the OH group in position 3. Here again, for example, there are no tertiary OH groups, which however are found in compound (II) of the present invention in positions 5 and 17. On page 6753 the authors focus on limitations of the oxidizing system described therein. Interestingly, a small structural difference entails unpredictable reactivity changes resulting in a low

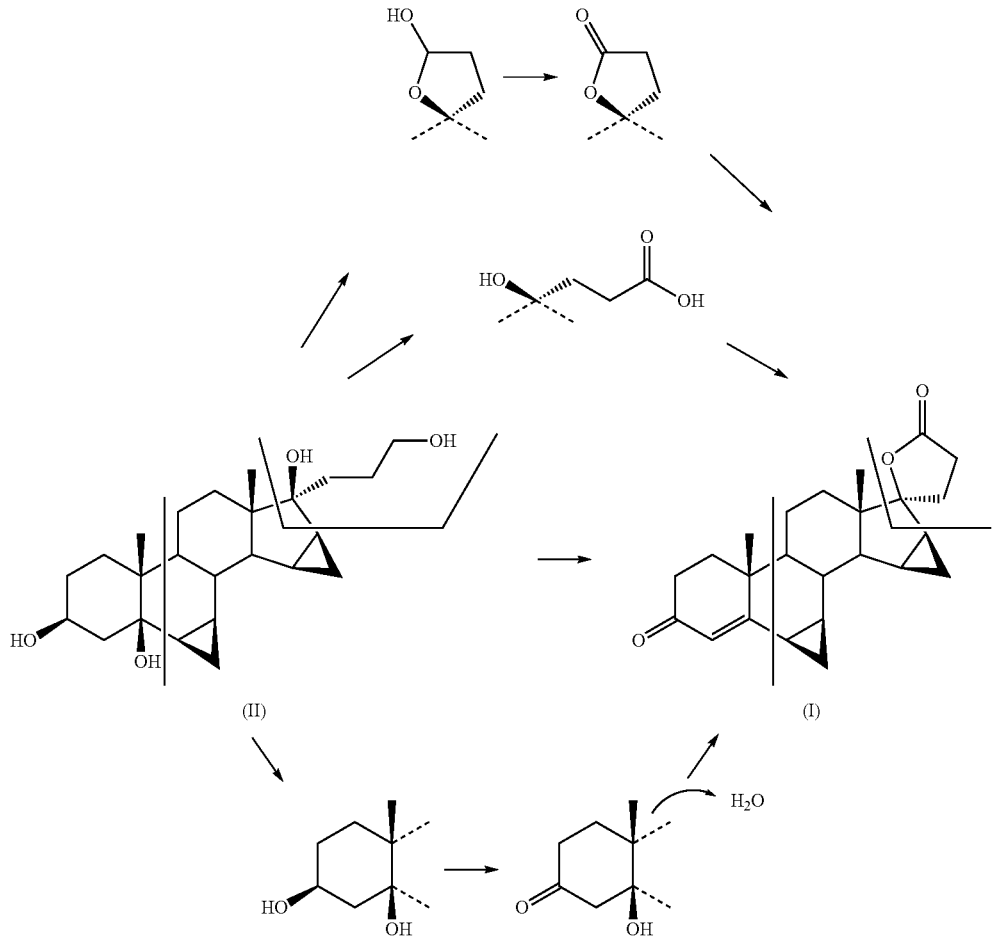

In particular, the tertiary OH group in position 17 should not be subjected to dehydration to generate the lactone ring whereas that in position 5 should be subjected to dehydration but only after oxidation of the secondary OH group in position 3. "Early" dehydration of OH group in position 5 would lead to the well-known formation of a diene, as described in the paper "Synthesis of α,β-unsaturated carboreaction rate and the formation of numerous by-products, as can be seen from a comparison discussed by the authors between the behavior observed in examples 6 and 7 of table 6 and molecule 5 in Figure 2, as well as from comparison of molecule 6 in Figure 2 with entry 10 in table 2. In addition, according to the authors, molecule 2 in Figure 2 is not subject to oxidation: it is readily apparent that in molecule 2, which does not undergo oxidation under the conditions as described in the paper, there is a $C_5$ lactone ring that can also be found in the compounds according to the present invention. Finally, on page 6751 of the paper, the catalyst is reported to be deactivated if the oxidation reaction is conducted at the boiling point of toluene, i.e. T=110-111° C.; by contrast, the present inventors noted that in the case of the invention not only this phenomenon does not take place, but an oxidation reaction carried out in toluene at a temperature ranging between 100° C. and the solvent boiling point is faster than when carried out at temperatures below 100° C. For all the above reasons, the skilled artisan would have not been motivated to apply the teaching from the paper by Nishimura et al. for the purposes of the present invention.

In contrast to the disclosures in European Patent EP 1828222 B1 and EP 918791 B8, in the present invention all reagents are loaded into the reaction container in a single step, without the need for further action in the course of the reaction, and all the above reactions take place over a single process phase.

The invention will be further illustrated by the following examples that are provided by way of illustration and are not intended to be limiting of the present invention. The reagents used in the examples are of common commercial availability and are used without prior purification.

Example 1

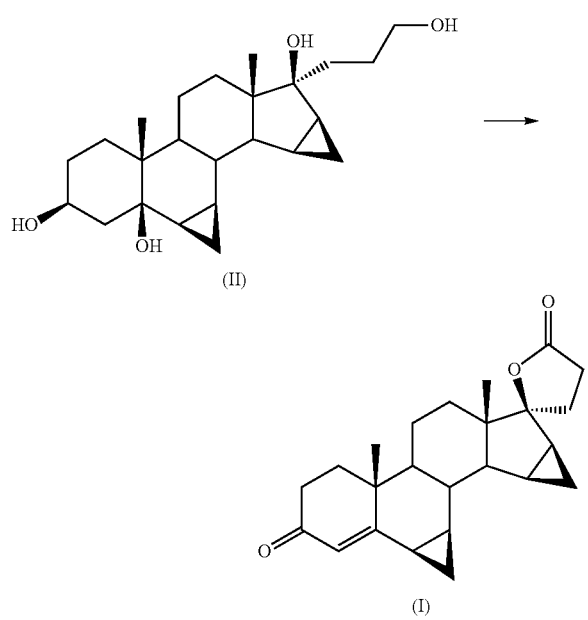

To a 50 ml flask at room temperature, 224 mg Pd(OAc)$_2$ (1 mmol), 10 ml toluene, 0.26 ml pyridine (255 mg) and 500 mg molecular sieves 3A are added. It is heated to 80° C. in oxygen atmosphere for 10 minutes.

Next 500 mg of 93% 17α-(3-hydroxypropyl)-6β,7β;15β,16β-dimethylene-5β-androstan-3β,5,17β-triol (II) are added. The reaction mixture is placed under stirring at 80-85° C. still in oxygen atmosphere for 16 h.

After this time, the organic phase is filtered on paper by washing the filter with methylene chloride and dry concentrated by distillation under reduced pressure (using a rotavapor apparatus).

The crude product following silica gel chromatography and drying to constant weight yields 346 mg drospirenone (HPLC purity as measured at 245 nm being 99.01%).

Example 2

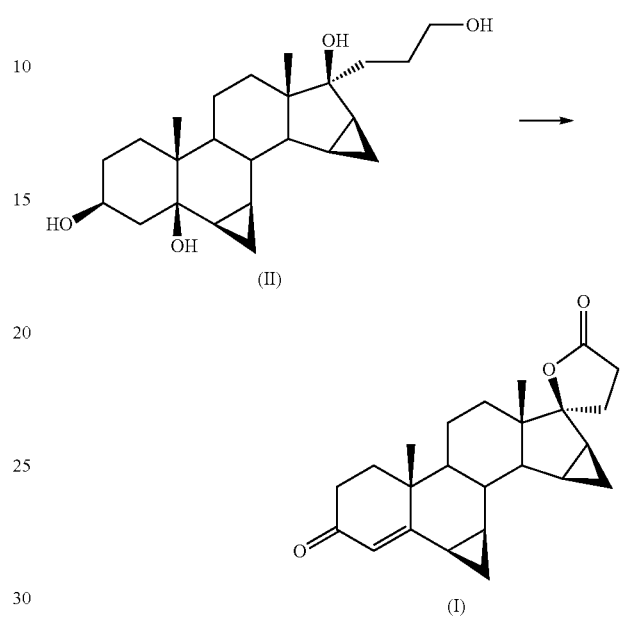

To a 1-liter flask at room temperature, 1.3 g Pd(OAc)$_2$, 300 ml toluene, 7.8 ml pyridine (7.65 g) and 15 g molecular sieves 3A are added.

It is heated to 80° C., internal pressure is adjusted first to 4 bar with nitrogen then to 4.5 bar with oxygen. The reaction is stirred under these conditions for 20 minutes while maintaining overall pressure at 4.5 bar using oxygen.

Next 15 g of 93% 17α-(3-hydroxypropyl)-6β,7β;15β,16β-dimethylene-5β-androstan-3β,5,17β-triol (II) are added. The reaction mixture is kept under agitation at 80° C. still in oxygen/nitrogen atmosphere at 4.5 bar for 64 h.

The organic phase is filtered by washing the filter with methylene chloride and dry concentrated (distillation on a rotavapor apparatus).

The crude product is crystallized using isopropyl acetate yielding after drying to constant weight 7.5 g drospirenone.

From mother liquors of crystallization another 1.5 g drospirenone are recovered by chromatography.

Example 3

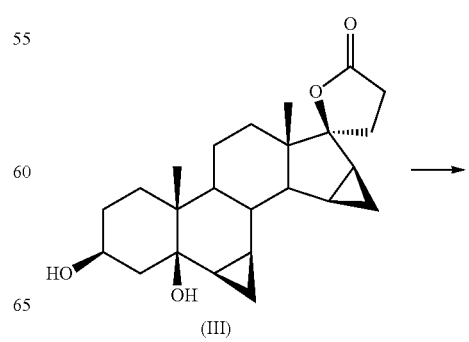

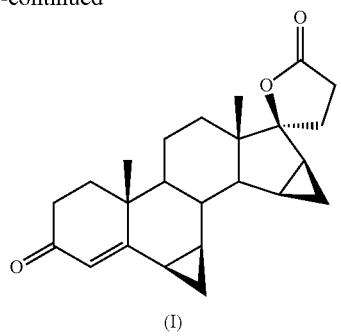

To a 50 ml flask at room temperature, 22 mg Pd(OAc)$_2$, 12 ml toluene, 0.4 ml (392 mg) pyridine and 1 g molecular sieves 3A are added.

It is heated to 80° C. in oxygen atmosphere for 10 minutes.

Next 772 mg 3β,5-dihydroxy-6β,7β,15β,16β-dimethylen-5β,17α-pregna-21,17-carbolactone (III) are added. The reaction mixture is placed under stirring at 80° C. still in oxygen atmosphere for 36 h.

The organic phase is filtered on paper by washing the filter with methylene chloride and dry concentrated (distillation on a rotavapor apparatus).

The crude product following silica gel chromatography and drying to constant weight yields 601 mg drospirenone (HPLC purity as measured at 245 nm being 98.04%).

Example 4

To a 2 liter flask at room temperature, 1.4 g Pd(OAc)$_2$, 1 liter toluene, 26.1 ml pyridine (25.6 g) and 50 g molecular sieves 3A in powder form are added. It is heated to 80° C. in oxygen atmosphere. The mixture is stirred under these conditions for 10 minutes while maintaining oxygen atmosphere.

Next 50 g of 93% 17α-(3-hydroxypropyl)-6β,7β;15β,16β-dimethylene-5β-androstan-3β,5,17β-triol (II) are added.

The reaction mixture is kept under agitation at 85° C. still in oxygen atmosphere for 64 h.

The organic phase is filtered by washing the filter with toluene and dry concentrated (distillation on a rotavapor apparatus).

The residue is crystallized using isopropyl acetate yielding 32.1 g drospirenone.

From mother liquors of crystallization another 4.5 g drospirenone are recovered by chromatography.

Example 5

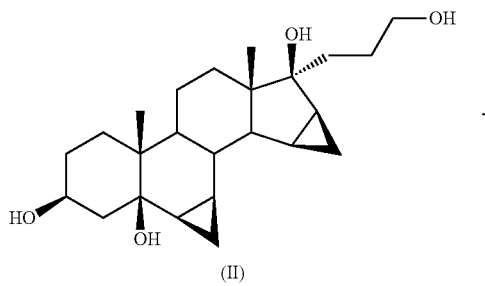

To a 250 ml flask at room temperature, 0.14 g Pd(OAc)$_2$, 100 ml toluene, 2.6 ml (2.55 g) pyridine and 5 g molecular sieves 3A in powder form are added. It is heated to 80° C. in oxygen atmosphere. The mixture is stirred under these conditions for 10 minutes while maintaining oxygen atmosphere.

Next 5 g of 93% 17α-(3-hydroxypropyl)-6β,7β,15β,16β-dimethylene-5β-androstan-3β,5,17β-triol (II) are added. The reaction mixture is kept under agitation at 100-110° C. still in oxygen atmosphere for 64 h (dark slurry).

The organic phase is filtered by washing the filter with toluene and dry concentrated (distillation on a rotavapor apparatus).

The residue is crystallized with isopropyl acetate yielding 3.1 g drospirenone, which, at HPLC analysis, show the presence of 1,2-dehydrodrospirenone as the major impurity.

The sample is hydrogenated in 30 ml tetrahydrofuran in the presence of 5% palladium on carbon (100 mg) while maintaining an excess hydrogen pressure of 1 to 1.5 bar at T=5° C.

After reaction completion the catalyst is filtered and the solvent removed under reduced pressure.

Recovery is 2.96 g drospirenone showing an amount of 1,2-dehydrodrospirenone lower than 0.10% based on further HPLC analysis.

Example 6

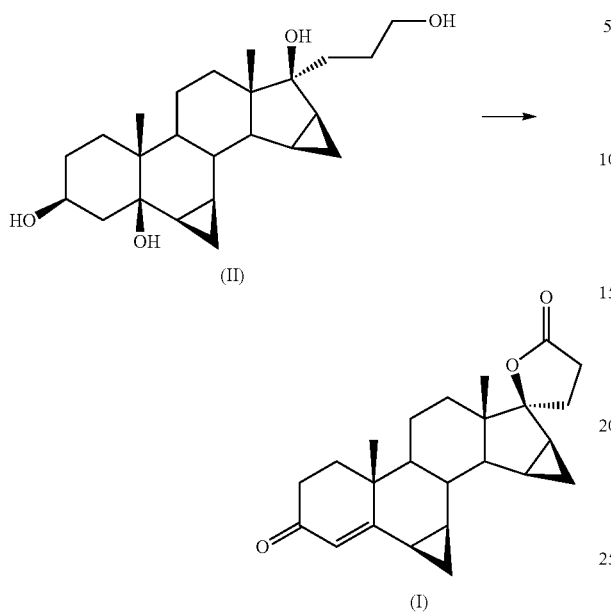

To a 3 liter flask at room temperature 1.4 g Pd(OAc)$_2$, 1 liter butyl acetate, 26.1 ml pyridine (25.6 g) and 50 g molecular sieves 3A in pellet form are added. It is heated to 80° C. in oxygen atmosphere. The mixture is stirred under these conditions for 20 minutes while maintaining oxygen atmosphere.

Next 50 g of 93% 17α-(3-hydroxypropyl)-6β,7β,15β, 16β-dimethylene-5β-androstan-3β,5,17β-triol (II) are added. The reaction mixture is kept under agitation at 80° C. still in oxygen atmosphere for 64 h (yellow slurry).

The organic phase is filtered by washing the filter with toluene and dry concentrated (distillation on a rotavapor apparatus).

The residue is crystallized using isopropyl acetate yielding 33.1 g drospirenone.

From mother liquors of crystallization another 4.1 g drospirenone are recovered by chromatography.

The invention claimed is:

1. Process for the preparation of drospirenone (I) comprising the single-step conversion of a compound selected from 17α-(3-hydroxypropyl)-6β,7β,15β,16β-dimethylen-5β-androstan-3β,5,17β-triol (II), alone or in a mixture with its lactols, and 3β,5-dihydroxy-6β,7β;15β,16β-dimethylen-5β,17α-pregna-21,17-carbolactone (III):

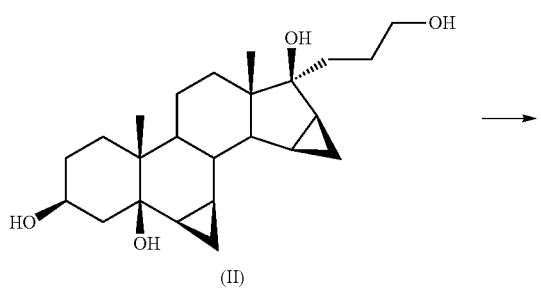

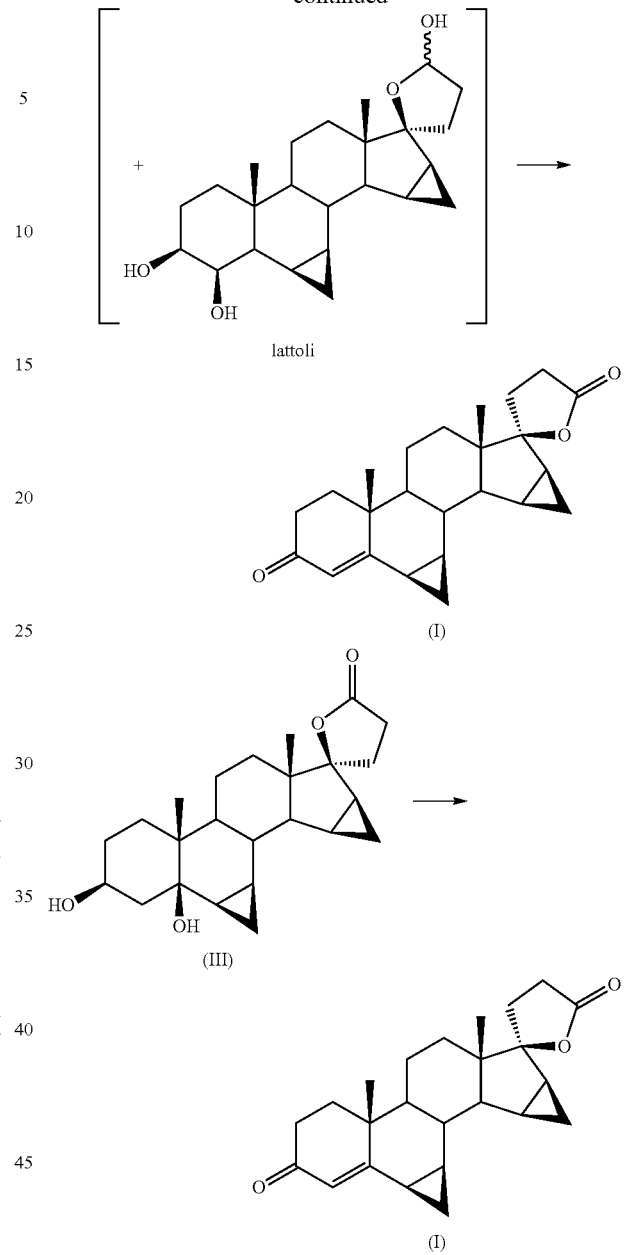

using oxygen gas in the presence of a palladium compound having the +2 oxidation state, an organic base and molecular sieves in an organic solvent inert under the reaction conditions, at a temperature between 60 and 140° C.

2. The process according to claim 1, wherein oxygen is used in form of pure oxygen, air, or mixtures of an inert gas and oxygen at a pressure between 1 and 10 bar.

3. The process according to claim 1, wherein said palladium compound is selected from acetate (Pd(C$_2$H$_3$O$_2$)$_2$), acetylacetonate (Pd(C$_5$H$_7$O$_2$)$_2$), trifluoroacetate (Pd(C$_2$O$_2$F$_3$)$_2$), hexafluoroacetylacetonate (Pd(C$_5$HO$_2$F$_6$)$_2$), propionate (Pd(C$_3$HSO$_2$)$_2$), chloride (PdCl$_2$), bromide (PdBr$_2$), iodide (PdI$_2$), cyanide (Pd(CN)$_2$), nitrate (Pd(NO$_3$)$_2$), sulfide (PdS), oxide (PdO) and hydroxide (Pd(OH)$_2$).

4. The process according to claim 1, wherein said palladium compound is used in amounts by weight ranging from 1% to 100% with respect to compound (II) or compound (III).

5. The process according to claim 1, wherein said organic base is selected from pyridine and its alkyl derivatives, triethylamine, aniline, pyrrolidine, DBU (1,8-Diazabicyclo[5.4.0]undec-7-ene), DBN (1,5-Diazabicyclo[4.3.0]non-5-ene), and cyclic compounds containing two or more nitrogen atoms, both aromatic and non-aromatic.

6. The process according to claim 1, wherein said organic base is used in amount by weight equal to or greater than 0.5 times the amount of palladium compound used.

7. The process according to claim 6, wherein the amount by weight of organic base is between 0.5 and 25 times as much as the amount of palladium compound used.

8. The process according to claim 1, wherein said molecular sieves have a pore diameter between 3 and 5 angstrom.

9. The process according to claim 1, wherein said organic solvent inert under reaction conditions is selected from methyl t-butyl ether, ethyl acetate, isopropyl acetate, butyl acetate, heptane, hexane, cyclohexane, toluene, xylene, 1,1-dichloroethane, 1,2-dichloroethane, 1,1,2-trichloroethane, tetrachloroethylene, methyl ethyl ketone, methyl isobutyl ketone, acetonitrile, dimethylformamide, dimethylacetamide, dimethyl sulfoxide, chlorobenzene, N-methyl-pyrrolidone or mixtures thereof.

10. The process according to claim 1, wherein said step is carried out for a period of time between 18 and 72 hours.

11. The process according to claim 1, wherein said step is carried out with palladium acetate, in the presence of pyridine as an organic base, using molecular sieves with pore diameter of 3 angstrom, at a temperature between 80 and 120° C., and for a period of time between 20 and 60 hours.

* * * * *

UNITED STATES PATENT AND TRADEMARK OFFICE
CERTIFICATE OF CORRECTION

| | |
|---|---|
| PATENT NO. | : 9,556,220 B2 |
| APPLICATION NO. | : 14/783830 |
| DATED | : January 31, 2017 |
| INVENTOR(S) | : Roberto Lenna |

It is certified that error appears in the above-identified patent and that said Letters Patent is hereby corrected as shown below:

In the Specification

Column 6, Line 3, change "Y. Ito et al., J. Org. Chem. 1978, Vol 43 (5) on page 1021," to --Y. Ito et al., J. Org. Chem. 1978, Vol 43 (5) on page 1011-1013,--

Signed and Sealed this
Ninth Day of October, 2018

Andrei Iancu
*Director of the United States Patent and Trademark Office*